US009975836B2

(12) United States Patent
Haritonov et al.

(10) Patent No.: US 9,975,836 B2
(45) Date of Patent: May 22, 2018

(54) METHOD OF PRODUCING C2-C4 CARBONYL COMPOUNDS

(71) Applicant: AKTSIONERNOE OBSCHESTVO "GAZPROMNEFT—MOSKOVSKY NPZ" (AO "GAZPROMNEFT-MNPZ"), Moscow (RU)

(72) Inventors: Alexandr Sergeevich Haritonov, Novosibirsk (RU); Konstantin Alexandrovich Dubkov, Novosibirsk (RU); Mihail Vladimirovich Parfenov, Novosibirsk (RU); Alexandr Stepanovich Noskov, Novosibirsk (RU); Valentin Nikolaevich Parmon, Novosibirsk (RU); Valery Alexandrovich Golovachev, St. Petersburg (RU); Andrei Vladimirovich Kleimenov, St. Petersburg (RU); Dmitry Olegovich Kondrashev, St. Petersburg (RU); Valentina Dmitrievna Miroshkina, Kstovo (RU); Petr Alexandrovich Abrashenkov, Moscow (RU)

(73) Assignee: AKTSIONERNOE OBSCHESTVO GAZPROMNEFT—MOSKOVSKY NPZ (AO "GAZPROMNEFT-MNPZ"), Moscow (RU)

( * ) Notice: Subject to any disclaimer, the term of this patent is extended or adjusted under 35 U.S.C. 154(b) by 0 days. days.

(21) Appl. No.: 15/540,044

(22) PCT Filed: Dec. 4, 2015

(86) PCT No.: PCT/RU2015/000848
§ 371 (c)(1),
(2) Date: Jun. 27, 2017

(87) PCT Pub. No.: WO2016/114687
PCT Pub. Date: Jul. 21, 2016

(65) Prior Publication Data
US 2017/0369410 A1    Dec. 28, 2017

(30) Foreign Application Priority Data

Jan. 12, 2015  (RU) ................................. 2015100715

(51) Int. Cl.
C07C 45/28    (2006.01)
(52) U.S. Cl.
CPC .................................. *C07C 45/28* (2013.01)
(58) Field of Classification Search
CPC ................................................... C07C 45/28
See application file for complete search history.

(56) References Cited

U.S. PATENT DOCUMENTS 8,420,866 B2    4/2013  Teles et al.

FOREIGN PATENT DOCUMENTS

| GB | 649680      | 9/1948 |
| GB | 649680 A    | 1/1951 |
| GB | 2 041 364 A | 9/1980 |
| RU | 2212396 C1  | 9/2003 |
| RU | 2227133 C2  | 4/2004 |
| RU | 2 258 059 C1| 8/2005 |
| WO | 2003/078370 A1 | 9/2003 |

OTHER PUBLICATIONS

RU 2212396 C1_English Abstract.
Espacenet English abstract of RU 2 258 059 C1.
Oxo Process, Kirk-Othmer Encyclopedia of Chemical Technology (4th Edition) vol. 17, pp. 465-474.
Rubailo V.L., Maslov S.A. Liquid-phase Oxidation of Unsaturated Compounds, M., Chemistry, 1989. p. 177, published in Russian and explained in the specification as describing non-catalytic oxidation of C2-C4 olefins using molecular oxygen according to a radical chain mechanism (see paragraph bridging pp. 2 and 3 of the specification and p. 4 lines 6-11).
Paushkin Ya. M., Petrochemical Synthesis Technology, Part 1. Hydrocarbon Raw Materials and Oxidation Products, M., Chemistry, 1973, published in Russian and explained in the specification as describing oxidation of saturated hydrocarbons by molecular oxygen without a catalyst (see p. 3 lines 4-10 of the specification).
Handbook of heterogeneous catalysis/Ertl G., Knozinger H., Weitkamp J.-Weinheim: VCH Verlagsgesellschaft mbH, 1997., vol. 5, p. 2284.
Kirk-Othmer Encyclopedia of Chemical Technology, 4th Ed., NY: John Wiley & Sons, 1994., V. 1. Acetaldehyde, p. 48.
Chernyshkova F., Mushenko D. Synthesis of Methyl Ethyl Ketone// Applied Chemistry. 1980, v. 53, No. 11, p. 2483, published in Russian and explained in the specification as describing attempts to use the Wacker Chemie process to convert olefins to carbonyl compounds (see p. 4 lines 3-5).
Chemical Encyclopedia: in 5 v.; v.3; Copper-Polymeric/Ed.: Knunyants I.L. (Ed.) et al., M.; Great Russian Encycl., 1992., p. 68, published in Russian and explained in the specification as describing preparation of methyl ethyl ketone from a butane-butylene mixture (see p. 4 lines 12-25).

(Continued)

*Primary Examiner* — Sikarl A Witherspoon
(74) *Attorney, Agent, or Firm* — Ladas & Parry LLP

(57) ABSTRACT

The invention relates to a method of producing carbonyl compounds, more particularly $C_2$-$C_4$ ketones and aldehydes. The method is based on the gas-phase oxidation by nitrous oxide of $C_2$-$C_4$ alkane-olefin mixtures, such as a butane-butylene fraction or a propane-propylene fraction, obtained by thermal and/or catalytic cracking, to produce $C_2$-$C_4$ ketones and aldehydes. The process is carried out under continuous flow conditions at a temperature of 300-550° C. and pressure of 1-100 atm, without prior isolation of individual olefins from the fractionation products and in the absence of a catalyst. The process provides for high productivity, high overall selectivity for ketones and aldehydes, and explosion-safe operation.

15 Claims, No Drawings

(56) References Cited

OTHER PUBLICATIONS

F.S. Bridson-Jones, G.D. Buckley, L.H. Cross, A.P. Driver. J. Chem. Soc. (1951) 2999.
Espacenet English abstract of RU 2227133 C2.
Starokon E.Y., Dubkov K.A., Babushkin D.E., Parmon V.N., Panov G.I. Liquid Phase Oxidation of Alkenes with Nitrous Oxide to carbonyl compounds//Adv. Synth. Catal., 2004., v. 346., p. 268.

METHOD OF PRODUCING C2-C4 CARBONYL COMPOUNDS

This application is a national phase entry under 35 USC 371 of international Patent Application No.: PCT/RU2015/000848 filed on 4 Dec. 2015, which claims priority from Russian Application No. 2015100715 filed on 12 Jan. 2015, the disclosures of which are incorporated in their entirety by reference herein.

This invention relates to the process of producing aliphatic carbonyl compounds, and more particularly, to a process of producing of ketones and aldehydes having from 2 to 4 carbon atoms ($C_2$-$C_4$) from mixtures of aliphatic $C_2$-$C_4$ olefins and alkanes, for example, from butane-butylene fractions and/or propane-propylene fractions of thermal or catalytic cracking, by the gas phase oxidation of such mixtures using nitrous oxide ($N_2O$).

$C_2$-$C_4$ aldehydes and ketones have various applications as valuable intermediate products in fine and basic organic synthesis. They are also widely used as solvents. In particular, acetaldehyde is used in the production of cellulose acetates, acetic and peroxyacetic acids, acetic anhydride, ethyl acetate, glyoxal, 2-ethylhexanol, alkylamines, butanol, pentaerythritol, alkylpyridines, 1,3-butylene glycol, chloral; and as a reducing agent in the manufacturing of mirrors.

Propionaldehyde is used in the production of propionic acid and its esters, methacrolein, metriol (the latter is used in the manufacturing of lubricants), photographic materials, in the synthesis of antibiotics, natural compounds (macrolides), and fragrances.

Acetone is widely used as a solvent, primarily for nitrates and cellulose acetates; due to its relatively low toxicity, it is also used in food and pharmaceutical industries; it is also used as a starting reagent for the synthesis of acetic anhydride, ketene, diacetone alcohol, oxide, mesityl, methyl isobutyl ketone, methyl methacrylate, diphenylolpropane, isophorone and many other compounds.

Butanal is used in the production of butanol, butyric acid and its anhydride, 2-ethylhexanol, 2-ethylhexane-1,3-diol (repellent and solvent), polyvinyl butyral, modified phenol-, urea- and aniline-formaldehyde resins. Isobutyraldehyde is used for the production of vitamin B5 (pantothenic acid), amino acids, for example, valine and leucine, isobutanol. Some products derived from isobutyric aldehyde are used as repellents (e.g., 2,2,4-trimethylpentane-1,3-diol, which is used against mosquitoes and fleas), mold inhibitors and insecticides.

Methyl ethyl ketone is used as a solvent for perchlorovinyl, nitrocellulose, and polyacrylic paint and varnish materials and adhesives, and printing inks; as well as for dewaxing of lubricating oils and de-oiling of paraffins (removal of oil and low-melting paraffin mixtures). Methyl ethyl ketone is used as an intermediate product in the production of methyl ethyl ketone peroxide (curing agent for polyester resins), sec-butyl amine, methyl ethyl ketone (antioxidant).

Carbonyl compounds (ketones and aldehydes) are generally obtained by oxo synthesis, oxidation of hydrocarbons or dehydrogenation of alcohols. However, these methods are not efficient enough. For example, the classic process of propylene hydroformylation with a mixture of CO and $H_2$ (oxo synthesis) is carried out at a pressure of 200-300 atm, in presence of toxic carbonyl complexes of Co, Rh, Ir (Oxo Process, Kirk-Othmer Encyclopedia of Chemical Technology (4th Edition) vol. 17, pp. 465-474). As a feedstock, individual alpha-olefins, for example, 1-butene, are used. When switching from butene-1 to butene-2, the rate of hydroformylation reaction decreases by 20-40 times, and when switching to isobutylene, it drops by 100 times. Synthesis of carbonyl compounds is accompanied by the formation of a significant number of by-products. For example, during the hydroformylation of propylene, a mixture is formed comprising butyric and isobutyric aldehydes, as well as n-butyl and isobutyl alcohols, butyl formate; butyric acid; ethers; acetals and the like. The selectivity for butyric and isobutyric aldehyde is 76-88%, with the propylene conversion ranging from 85 to 90% (RU No. 2258059, C07C47/02, Aug. 10, 2005). Disadvantages of this method are: the necessity of using individual olefins, partial hydrogenation of the starting propylene, the complexity of isolating the desired products from the final reaction mixture. It should also be noted that oxo synthesis is unsuitable for obtaining ketones.

Non-catalytic oxidation of $C_2$-$C_4$ olefins, using molecular oxygen, proceeds according to radical chain mechanism involving the intermediate formation of peroxide radicals. The reaction leads to the formation of alcohols, aldehydes, ketones, acids, epoxides, products of polymerization and of oxidative cleavage of $C=C$ bonds, as well as products of deep oxidation (Rubailo V. L., Maslov S. A. Liquid-phase Oxidation of Unsaturated Compounds, M., Chemistry, 1989. p. 177, published in Russian). Saturated hydrocarbons are also oxidized relatively easily by molecular oxygen, without using any catalyst, both in liquid and gas phases. Oxidation of $C_2$-$C_4$ alkanes results in methanol, formaldehyde, acetaldehyde, acetone, ethanol, glycols, organic acids, carbon oxides and water. In this case, the proportion of aldehydes and ketones usually does not exceed 30-40%. The difficulty in isolating the target products from the alkane oxidation reaction mixture, makes this technology unprofitable (Paushkin Ya. M., Petrochemical Synthesis Technology, Part 1. Hydrocarbon Raw Materials and Oxidation Products, M., Chemistry, 1973, p. 448, published in Russian). It is obvious that non-selective oxidation of $C_2$-$C_4$ alkane-olefin mixtures by molecular oxygen, should result in formation of oxygenates of even more complex composition than the oxidation of individual $C_2$-$C_4$ olefins or individual $C_2$-$C_4$ alkanes. This makes it practically impossible to use molecular oxygen to obtain aldehydes and ketones from alkane-olefin mixtures.

A process of catalytic liquid-phase oxidation of olefins with oxygen, using palladium and copper (II) chlorides as a catalyst is known (Handbook of heterogeneous catalysis/Ertl G., Knozinger H., Weitkamp J.-Weinheim: VCH Verlagsgesellschaft mbH, 1997., vol. 5, p, 2284). This method is most widely used for the synthesis of acetaldehyde from ethylene (Wacker Chemie company process). The process is carried out in one or two stages in HCl medium at 100-130° C. and pressure of up to 11 atm. Under these conditions, selectivity for acetaldehyde reaches 94-95%, with ethylene conversion being in the range of 35-100%. By a similar method, acetone is obtained from propylene, with a yield of about 90%, on an industrial scale (Kirk-Othmer Encyclopedia of Chemical Technology, 4th Ed., NY: John Wiley & Sons, 1994., V. 1. Acetaldehyde, p. 48). The main disadvantages of this method are: formation of a significant amount of chlorine-containing by-products, difficulty of isolating and purifying the target products, presence of acidic effluents, as well as high corrosivity of chloride solutions, which results in the necessity of using equipment made from special materials.

There have been attempts made to use the Wacker Chemie process to convert other olefins to carbonyl compounds, for example, to convert n-butylenes to methyl ethyl ketone (Chernyshkova F., Tvlushenko D. Synthesis of Methyl Ethyl Ketone"//Applied Chemistry. 1980, v. 53, no. 11, p. 2483, published in Russian). However, the process of oxidation of 1-butene to methyl ethyl ketone has not yet been carried out on an industrial scale, because of the difficulties in separating the products. It should be noted that n-butylenes, especially non-terminal ones, have a significantly lower reactivity in comparison with ethylene and propylene, which significantly reduces the efficiency of such process (Rubailo V. L., Maslov S. A. Liquid-phase Oxidation of Unsaturated Compounds/M.: Chemistry, 1989, p. 177, published in Russian).

A method is known for the preparation of methyl ethyl ketone from a butane-butylene mixture, without preliminary isolation of olefins therefrom (Chemical Encyclopedia: in 5 v.; Copper-Polymeric/Ed.: Knunyants I. L. (Ed.) et al., M.; Great Russian Encycl., 1992., p. 68, published in Russian; GB2041364A). The first stage of the process is the hydration of the butane-butene fraction in the presence of 70-85% $H_2SO_4$ at 30-40° C. and pressure of approximately 0.1 Mpa, resulting in 2-butanol with an intermediate formation of 2-butylsulfate. 2-Butanol is isolated by rectification, and in the second stage, it is converted to methyl ethyl ketone by dehydrogenation at 400-500° C. ('ZnO on pumice' catalyst, zinc-copper catalyst) or oxidized by dehydrogenation at 500° C. in the presence of Ag on pumice' catalyst. The selectivity for hydration of butenes is 80-85%, the selectivity for dehydrogenation of 2-butanol is about 99%, the selectivity for oxidative dehydrogenation is 85-90%. Disadvantages of the process are the following: formation of a large amount of effluents at the hydration stage, high energy costs associated with the necessity to concentrate $H_2SO_4$, because of its dilution to 35% during the hydration.

GB 649680 (C07C45/34, Sep. 22, 1948) describes the process for the preparation of carbonyl compounds, carried out by reaction of nitrous oxide with olefins, in a static autoclave at a temperature of 250-500° C. and pressure of up to 1000 atm. According to this method, in particular, it is possible to produce propanal and acetone by oxidizing propylene at a temperature of 250-300° C. and pressure of 500 atm for 1.5-2 hours. This method is described in more details in the article [F. S. Bridson-Jones, G. D. Buckley, Cross, A. P. Driver. J. Chem. Soc. (1951) 2999]. The disadvantage of this method is the low selectivity, extremely harsh processing conditions, including feeding liquid nitrous oxide to the reactor, which, as the authors themselves note, led to an uncontrolled behavior of the process, a sharp increase in pressure and a destruction of the equipment in a number of experiments.

Patent RU No. 2227133 (C07C49/04, Apr. 20, 2004) describes a process for the preparation of carbonyl compounds (acetone, propionic aldehyde and acetaldehyde in a molar ratio of 1:0.4:0.15) by liquid phase oxidation of propylene with nitrous oxide in a solution of mesitylene. In this case, the oxidation is carried out in the presence of an inert diluent gas, in a static autoclave reactor at a temperature of up to 350° C. and pressure of $N_2O$ up to 100 atmospheres. This method is described in more detail in Starokon E. Y., Dubkov K. A., Babushkin D. E., Parmon V. N., Panov G. I. Liquid Phase Oxidation of Alkenes with Nitrous Oxide to carbonyl compounds"//Adv. Synth. Catal., 2004., v. 346., p. 268, where examples of the oxidation of ethylene, propylene and butylenes by nitrous oxide in a benzene solution are provided.

The method of liquid-phase oxidation of isobutene analogues (1,1-disubstituted olefins) by nitrous oxide is known (U.S. Pat. No. 8,420,866, C07C45/28, Apr. 16, 2013), the said method being carried out at temperatures up to 350° C. and pressures up to 1000 atmospheres, and for increasing selectivity for ketones, the oxidation in this method is carried out in the presence of a protic solvent.

However, the methods described above for the preparation of carbonyl compounds by liquid phase oxidation of olefins with nitrous oxide have a number of disadvantages. In particular, since the reaction is carried out in an autoclave reactor, an increase in temperature to accelerate the reaction is accompanied by a significant increase in pressure in the reaction system, resulting from olefin, solvent and nitrous oxide vapors. Carrying out the process in an autoclave in a static mode results in a necessity of periodic shutdowns of the reactor, in order to reload it, which drastically reduces the efficiency of the equipment usage. In addition, during the reaction, the solvent can also undergo chemical transformations. For example, according to the data by Starokon E. Y., Dubkov K. A., Babushkin D. E., Parmon V. N., Panov G. I. Liquid Phase Oxidation of Alkenes with Nitrous Oxide to Carbonyl Compounds//Adv. Synth. Catal., 2004, v. 346, p. 268, benzene used as a solvent is partially converted to cycloheptatriene during the oxidation of alpha-olefins.

The present invention discloses a process for the preparation of carbonyl compounds ($C_2$-$C_4$ aldehydes and ketones) that does not have the drawbacks listed above.

The technical result of the invention consists in the process, according to the present invention, providing high performance, high total selectivity for ketones and aldehydes, and explosion safety.

The process of obtaining $C_2$-$C_4$ carbonyl compounds, in particular $C_2$-$C_4$ aldehydes and ketones, is carried out in a gaseous phase by reacting nitrous oxide with a mixture of aliphatic $C_2$-$C_4$ olefins and alkanes at a temperature of 300-550° C. and pressure of 1-100 atm.

Gaseous fractionation products of thermal and/or catalytic cracking process are used as the starting alkane-olefin mixture with no preliminary isolation of individual olefins from the fractionation products.

Butane-butylene fraction of thermal and/or catalytic cracking process is used as the starting alkane-olefin mixture.

Propane-propylene fraction of thermal and/or catalytic cracking process is used as the starting alkane-olefin mixture.

A fraction of thermal and/or catalytic cracking process enriched in ethylene is used as the starting alkane-olefin mixture.

Butane-butene mixture enriched with butene-2 is used as the starting alkane-olefin mixture.

A mixture containing $C_2$ and/or $C_3$ and/or $C_4$ olefins with $C_1$ and/or $C_2$ and/or $C_3$ and/or $C_4$ alkanes, with any ratios, is used as the starting alkane-olefin mixture.

The starting alkane-olefin mixture may comprise other hydrocarbons as impurities, caused by the process of its preparation.

Nitrous oxide may comprise other gases, the presence of which is associated with the process for its preparation.

The oxidation process of the alkane-olefin mixture is carried out in a single flow-type reactor, without recycling the reaction mixture, with nitrous oxide conversion being at least 90%, preferably 99%, even more preferably with a complete nitrous oxide conversion.

To achieve an olefin conversion of at least 90%, the oxidation of the alkane-olefin mixture is carried out in several stages, using several oxidation reactors with independent feeding of nitrous oxide at each stage, and with an independent separation of the reaction products from the reaction mixture after each oxidation reactor.

To achieve an olefin conversion of at least 90%, the oxidation of the alkane-olefin is carried out in several stages, using several oxidation reactors with independent feeding of nitrous oxide at each stage, and with an intermediate partial cooling of the reaction mixture, but without separating the reaction products from the reaction mixture after the intermediate oxidation reactors.

The disclosed process is carried out by gas-phase oxidation of $C_2$-$C_4$ alkane-olefin mixtures, for example, hydrocarbon gases of thermal and/or catalytic cracking process with no preliminary separation thereof, into individual components, with nitrous oxide ($N_2O$) in a flow mode. Carrying the process out in a gas phase in the flow mode, makes it possible to easily control the reaction rate by adjusting the reaction temperature and pressure that, in this case, are not limited by the phase equilibrium conditions and can vary independently.

In a specific embodiment, fractionation products of the reaction mixture of thermal and/or catalytic cracking process are used as a feedstock, for example a propane-propylene fraction and/or a butane-butylene fraction. Butane-butylene fraction can be as a feedstock as well, after extracting isobutene esterification product therefrom, using methanol and/or ethanol (in this case, the reaction mixture for oxidation with nitrous oxide can be used without removing methanol and/or ethanol). For the synthesis of methyl ethyl ketone, butane-butylene fraction enriched in butene-2 is preferable. The use of butane-butylene mixture as a feedstock, instead of individual butenes, makes it possible to reduce material costs substantially, as the very energy-consuming process of isolating individual components is eliminated. Nitrous oxide can be used both in pure form and with impurities, the presence of which is due to the method of its preparation. The olefins content in the $C_2$-$C_4$ mixture can vary within a wide range, and the lower limit of the olefin content in the mixture is determined only by economic reasons.

According to the claimed process, the starting alkane-olefin mixture of $C_2$-$C_4$ hydrocarbons is mixed with nitrous oxide, in a ratio that eliminates the possibility of formation of an explosive mixture. Hydrocarbon-rich mixtures with nitrous oxide are explosion-proof under normal conditions. Since the concentration limits expand with increasing temperature and pressure, it is recommended to oxidize the butane-butene mixture at a concentration of nitrous oxide in the mixture at no more than 30 vol. %.

According to the present invention, the gas-phase oxidation of a mixture of aliphatic $C_2$-$C_4$ olefins and alkanes to aldehydes and ketones with nitrous oxide is carried out without using a catalyst in the flow-type reactor at a temperature of 300 to 550° C., pressure of 1 to 70 atm and using a contact time (residence time of the mixture in the reactor) from 0.01 minutes to 60 minutes (based on normal conditions). It is preferable to carry out the process at a temperature of 350 to 450° C., pressure of 10 to 50 atm, and a contact time of 0.2 to 20 min (for normal conditions). The process can be carried out in isothermal or adiabatic mode, in a single or several stages.

Under the disclosed conditions, $C_2$-$C_4$ olefins are oxidized by nitrous oxide and form $C_2$-$C_4$ aldehydes and/or ketones, and the product of the conversion of $N_2O$ is molecular nitrogen. During the oxidation of mixtures containing terminal olefins (ethylene, propylene, 1-butene, isobutene), additional cyclopropane derivatives are additional valuable products of the $C_2$-$C_4$ olefins conversion. For example, when propane-propylene mixtures are oxidized, methylcyclopropane ($C_4$ hydrocarbon) is formed, and dimethylcyclopropanes and ethylcyclopropane ($C_5$ hydrocarbons) are formed during the oxidation of butane-butene mixtures. Since under the disclosed conditions, nitrous oxide reacts only with olefins, and does not react with alkanes and reaction products (aldehydes, ketones, cyclopropane derivatives), the oxidation can be carried out to achieve high degrees of olefin conversion, with no significant reduction of selectivity for the target products. In particular, this makes it possible to carry out the oxidation process in several stages (using several oxidation reactors) without an intermediate isolation of the reaction products from the reaction mixture.

In accordance with the invention, three basic options for organizing the oxidation process are possible. In the first embodiment, the oxidation of a $C_2$-$C_4$ hydrocarbon mixture comprising an olefin is carried out in a flow-type reactor in a single step. This variant of the process is preferable for the oxidation of feedstock hydrocarbon mixtures having an olefin content lower than 30 vol. %. In the second embodiment, the oxidation process is carried out in several stages using two or more oxidation reactors, in this case, after each oxidation reactor, the carbonyl products are isolated from the reaction mixture, and nitrous oxide is added to the mixture before feeding the later to the next reactor. In the third embodiment, the oxidation process is also carried out in several stages, but without the intermediate isolation of the carbonyl products. In this case, the reaction mixture is partially cooled after each reactor except the last one, and nitrous oxide is fed into the reaction mixture independently before each of the subsequent reactors. In this case, nitrous oxide is fed with no preheating and can be used to partially cool the reaction mixture. The second and third variants of the process are preferable for the oxidation of alkane-olefin mixtures having an olefin content higher than 30 vol. %.

According to the first embodiment of the process, the gas-phase oxidation of the $C_2$-$C_4$ alkane-olefin mixture, for example the butane-butene fraction of catalytic and/or thermal cracking process, or any other mixture of $C_2$-$C_4$ olefins with alkanes is carried out in a single step, under the conditions able to provide at least 90% conversion of nitrous oxide, preferably at least 99% conversion, and at least 50% conversion of the olefins, preferably at least 90% conversion. The oxidation process is carried out in such a way that the adiabatic heating of the reaction mixture does not exceed 200° C., preferably 120° C. It is possible to use both an adiabatic reactor and a reactor with a partial removal of the reaction heat. The reaction mixture leaving the reactor is cooled. Nitrogen gas ($N_2O$ conversion product) is blown off, and the condensed products are passed to a rectification step. Other known separation techniques, such as extractive distillation, recrystallization, etc., can be used to isolate the carbonyl compounds. It should be noted that during the oxidation of olefins with nitrous oxide, no water is formed. The absence of water in the reaction mixture facilitates the isolation of individual carbonyl compounds by rectification, since water forms azeotropic mixtures with most of them. A hydrocarbon mixture with unreacted olefin residues and conversion by-products can be used as a component of liquefied gas fuels. Cyclopropane derivatives ($C_5$ fraction in the case of butene oxidation), having an octane number corresponding to 103-104 RON, can be used for formulating motor gasoline fuels.

According to the second embodiment of the process, the oxidation of the $C_2$-$C_4$ alkane-olefin mixture comprising more than 30 vol. % of olefins, for example, butane-butene fraction of catalytic and/or thermal cracking process with butene content above 30 vol. %, or any other highly concentrated mixture of $C_2$-$C_4$ olefins with alkanes, is carried out in several stages. The number of stages depends on the concentration of olefins in the feedstock hydrocarbon mixture. The higher the olefin concentration, the greater the number of stages. When the olefin concentration in the feedstock mixture is approximately 50%, at least 2 reactors are necessary to ensure their conversion above 90%, and when the olefin concentration is 80%, at least 3 oxidation reactors are necessary. According the second embodiment, after each of the reactors (except the last one), the reaction mixture is cooled, nitrogen is purged and the desired reaction products are isolated. The remaining reaction mixture, after mixing with nitrous oxide and heating to a predefined temperature, is fed to the next reactor. The oxidation process is carried out under conditions such that the conversion of nitrous oxide in each of the intermediate reactors is at least 50%, preferably 90%, more preferably at least 99%. The conversion of nitrous oxide in the last reactor should be at least 90%, preferably at least 99%. To maintain the performance of the volume unit of each subsequent reactor at the performance level of the volume unit of the first reactor, it is advisable to incrementally increase the temperature of the reaction mixture at the inlet to each subsequent reactor by 20-60° C. The oxidation process in each of the reactors is preferably carried out, in such a way that the adiabatic heating of the reaction mixture does not exceed 200° C., preferably 120° C. The reaction mixture after the last reactor is cooled to achieve condensation and passed to rectification, in order to isolate the desired products.

According to the third embodiment of the process, the oxidation is carried out in a manner similar to embodiment 2, i.e., in several stages, but the products are not isolated after each of the reactors, except for the last one. Nitrous oxide is added to the reaction mixture before each of the reactors following the first. The mixture is partially cooled to a temperature allowing a $N_2O$ conversion in the subsequent reactor to be at least 90%, more preferably 99%, and an olefin conversion to be at least 50%, preferably at least 90%.

The technical essence of the invention is illustrated by the following examples and tables.

EXAMPLE 1

Butane-butene fraction of catalytic cracking process having butenes content of 87.4% by volume and butanes content of 12.1% (Table 1, Mixture 1) is mixed with nitrous oxide in a ratio of 9:1. The reaction mixture at a pressure of 1 atm. is passed through a stainless steel reactor having a volume of 2.5 cm$^3$, in which temperature of 400° C. is maintained. The feed rate of the mixture is 25 cm$^3$/min (at normal conditions). The results of the experiment are given in Table 2. Here, the reaction temperature (T), nitrous oxide conversion ($X_{N2O}$), total olefin conversion ($X_R$), total ketone and aldehyde performance (Pr) and total selectivity for carbonyl products ($S_\Sigma$) are provided. One can see that the total selectivity for carbonyl compounds, considering the accuracy of the selectivity determination, approaches 100%. The main product of the reaction is methyl ethyl ketone (MEK), which is formed with a selectivity of 44.8%. Along with MEK, acetone (A) with a selectivity of 17.5%, propanal (PA) with a selectivity of 17.5%, acetaldehyde (AA) with a selectivity of 11.3%, isobutanal (i-BA) with a selectivity of 4.6%, and butyraldehyde (BA) with a selectivity of 4.3% are formed. The main by-products are C$_5$ hydrocarbons: dimethyl- and ethyl-cyclopropanes.

EXAMPLES 2-4

The reaction is carried out similarly to Example 1, with the main difference being that the reaction temperature is adjusted at 450° C. (Table 2, Example 2), 500° C. (Table 2, Example 3) and 550° C. (Table 2, Example 4). These experiments show that an increase in the temperature leads to a significant acceleration of the reaction: the performance of the volume unit of the reactor increases by more than 40 times. The total selectivity for carbonyl compounds remains above 94% with an increase in temperature from 450° C. to 500° C., and only the increase in temperature to 550° C. leads to a decrease in the total selectivity for carbonyl compounds to 77%.

EXAMPLE 5

The experiments are carried out in the same manner as in Example 1, with the difference being that the temperature in the reactor is maintained at 350° C., and the pressure of the reaction mixture is set at 5 atm. One can see from Table 2 that, despite the temperature decrease, in comparison with Example 1, an increase in pressure in the reactor results in an increase in the reactor performance, in what concerns the carbonyl compounds. At the same time, there is an increase in the selectivity for MEK by almost 10% (from 45 to 54%).

EXAMPLES 6-8

The test is carried out similarly to Example 5, with the difference being that the reaction temperature is set at 400° C. (Table 2, Example 6), 450° C. (Table 2, Example 7) and 500° C. (Table 2, Example 8). With an increase in temperature from 400° C. to 500° C., the performance per unit volume of the reactor increases by more than 7 times. In this case, the selectivity for the MEC formation essentially does not change with the increase in the temperature. With increasing temperature, the total selectivity for carbonyl compounds decreases from 100 to 89% due to the formation of cyclopropanes (C5) and other products. At 500° C., complete conversion of nitrous oxide is observed.

EXAMPLE 9-12

The experiment is carried out similarly to Example 5, with the difference being that the pressure of the reaction mixture in the reactor is set at 10 atm (Table 2, Example 9), 20 atm (Table 2, Example 10), 50 atm (Table 2, Example 11) and 70 atm (Table 2, Example 12). Increasing the pressure of the reaction mixture from 10 to 70 atm is accompanied by an increase in the performance of the reactor volume unit by more than 100 times, from 7.4 g/l h to 770 g/l h, reaching the level of the most effective industrial petrochemical processes. As the pressure increases, the conversion of nitrous oxide increases from 43 to 99%, with a decrease in the total selectivity for carbonyl compounds from 94 to 76%, while the selectivity for MEC decreases insignificantly from 46 to 40%.

EXAMPLE 13

The test is carried out similarly to Example 5, with the difference being that the butane-butene fraction of catalytic cracking process (composition 1) with butenes content of 87.4% by volume and butanes content 12.1% is mixed with nitrous oxide in a ratio of 7:3. An increase in the content of nitrous oxide in the reaction mixture from 10 mol. % to 30 mol. % is accompanied by an increase in the performance of the reaction volume unit by more than 2 times with an insignificant decrease in the total selectivity for carbonyl compounds (less than 2%).

EXAMPLE 14

The test is carried out in a manner similar to that of Example 13, with the difference being that the temperature of the reaction mixture is maintained at 450° C., Table 2 shows that the increase in temperature leads to an increase in the performance of the reactor volume unit by more than 2 times from 7.4 g/l h to 16.4 g/l h. At the same time, the conversion of nitrous oxide increases by 2.5 times, approaching 80%, while maintaining the total selectivity for carbonyl compounds at 90%.

EXAMPLES 15-20

Examples 15-20 describe the effect of the composition of the alkane-olefin mixture on the production of $C_2$-$C_4$ aldehydes and ketones. The composition of the products of thermal and/or catalytic cracking is highly dependent on the petrochemical feedstock, the process conditions, the nature of the catalyst, and can vary widely. In the stepwise oxidation of alkane-olefin mixtures, with the partial conversion of the olefin, the composition of the reaction mixture will change as the transition from the previous to the subsequent reactor takes place. Table 1 shows the composition of $C_2$-$C_4$ butane-butene mixtures used to prepare carbonyl compounds.

Mixture 1 corresponds to harsh catalytic cracking conditions. The results of its oxidation are provided above (Examples 1-15). Mixture 2 corresponds to mixture 1, partially converted according to the embodiment 2 of the process, with the recovery of the reaction products from the reaction mixture. Mixture 3 corresponds to mixture 1, partially converted according to the embodiment 2 of the process, with the recovery of the reaction products from the reaction mixture, where the conversion of the olefins is higher than in mixture 2.

Mixture 4 corresponds to milder cracking conditions. Mixture 5 is enriched in butene-2, and Mixture 6 corresponds to butane-butene fraction of thermal cracking, Mixture 7 corresponds to butane-butene fraction of catalytic cracking, from which isobutene has been recovered by means of esterification thereof, with methanol. A description of the experimental conditions and the obtained results is provided in Table 3 (Examples 15-20). One can see that varying the process conditions makes it possible to efficiently perform the oxidation of butane-butene with low olefin content in the mixture. With a relatively high performance in what concerns the carbonyl compounds, the total selectivity for aldehydes and ketones exceeds 80%.

EXAMPLES 21-30

Examples 21-30 describe the oxidation of the propane-propylene fraction of catalytic cracking process. The experimental conditions and results are provided in Table 4. The main products of the oxidation are carbonyl compounds: acetone (A), acetaldehyde (AA), and propanal (PA). The total selectivity for carbonyl compounds varies from 71 to 95% depending on the reaction conditions. The maximum performance reaches 10 g/l h with the conversion of nitrous oxide being 75%.

The disclosed process provides high productivity, high total selectivity for ketones and aldehydes, and explosion safety.

TABLE 1

Composition of the starting butane-butylene mixtures

| | Mixture composition, % by volume | | | | | | |
|---|---|---|---|---|---|---|---|
| Component | Mixture 1 | Mixture 2 | Mixture 3 | Mixture 4 | Mixture 5 | Mixture 6 | Mixture 7 |
| Methane | — | | | — | — | — | 0.21 |
| Ethane | — | | | — | — | — | 0.07 |
| Ethylene | — | — | — | — | — | — | 0.05 |
| Propane | — | | | — | — | 0.4 | 1.3 |
| Propylene | — | | | — | — | 4.3 | 0.1 |
| Isobutane | 1.6 | 3.8 | 6.4 | 0.6 | 1.57 | 1.1 | 50.3 |
| Butane | 10.5 | 71.0 | 80.3 | 41.5 | 45.3 | 55.9 | 9.92 |
| Butene-1 | 32.9 | 9.5 | 5.0 | 25.6 | 5.6 | 13 | 14.34 |
| Butadiene | 0.5 | 0.1 | 0.1 | 0.3 | 0.486 | 0.3 | 0.23 |
| t-Butene-2 | 24.9 | 7.2 | 3.8 | 15.3 | 24.9 | 11.6 | 12.8 |
| Isobutene | 15.1 | 4.3 | 2.3 | 3.2 | 7.7 | 5.3 | 2.9 |
| c-Butene-2 | 14.5 | 4.2 | 2.2 | 13.5 | 14.45 | 8.1 | 7.8 |
| Sum of olefins, % | 87.4 | 25.1 | 13.2 | 57.6 | 52.7 | 42.3 | 37.95 |

TABLE 2

Gas phase oxidation of butane butylene mixture (BBM) with a butene content of 87.4% by volume and a butane content of 12.1% (Mixture 1 in Table 1) by nitrous oxide. Reaction conditions: flow-type reactor 25 cm$^3$, temperature 300-550° C., pressure 1-20 atm; feedstock mixture: 10-30 mol % $N_2O$, 90 mol % BBM; the volume flow rate of the mixture is 25 cm$^3$/min (for normal conditions)

| No | P, atm. | T, ° C. | $X_{N2O}$, % | $X_R$, % | Pr, g/l h | Selectivity, S, % | | | | | | | | $S_\Sigma^{b)}$, % |
|---|---|---|---|---|---|---|---|---|---|---|---|---|---|---|
| | | | | | | C5 | AA | PA | i-BA | A | BA | MEK | Other products | |
| 1 | 1 | 400 | 0.7 | 0.1 | 0.1 | 0.0 | 11.3 | 17.5 | 4.6 | 17.5 | 4.3 | 44.8 | 0.0 | 100 |
| 2 | | 450 | 2.9 | 0.4 | 0.5 | 0.0 | 5.1 | 17.4 | 6.2 | 14.6 | 5.3 | 51.4 | 0.0 | 100 |
| 3 | | 500 | 10.6 | 1.4 | 1.8 | 0.0 | 7.9 | 16.0 | 5.8 | 13.3 | 2.3 | 48.5 | 6.2 | 93.8 |
| 4 | | 550 | 33.5 | 4.2 | 4.4 | 0.0 | 6.0 | 13.2 | 4.6 | 12.4 | 1.3 | 39.5 | 23.0 | 77.1 |
| 5 | 5 | 350 | 3.0 | 0.4 | 0.52 | 0.0 | 11.0 | 15.0 | 4.2 | 13.2 | 3.1 | 53.5 | 0.0 | 100 |
| 6 | | 400 | 14.0 | 1.7 | 2.3 | 0.0 | 12.5 | 16.3 | 4.8 | 12.4 | 3.2 | 50.8 | 0.0 | 100 |
| 7 | | 450 | 47.7 | 6.1 | 7.8 | 4.3 | 12.1 | 14.9 | 5.0 | 12.8 | 2.6 | 47.7 | 0.7 | 95.1 |

TABLE 2-continued

Gas phase oxidation of butane butylene mixture (BBM) with a butene content of 87.4% by volume and a butane content of 12.1% (Mixture 1 in Table 1) by nitrous oxide. Reaction conditions: flow-type reactor 25 cm$^3$, temperature 300-550° C., pressure 1-20 atm; feedstock mixture: 10-30 mol % N$_2$O, 90 mol % BBM; the volume flow rate of the mixture is 25 cm$^3$/min (for normal conditions)

| No | P, atm. | T, ° C. | $X_{N2O}$, % | $X_R$, % | Pr, g/l h | Selectivity, S, % | | | | | | | | $S_\Sigma^{b)}$, % |
|---|---|---|---|---|---|---|---|---|---|---|---|---|---|---|
| | | | | | | C5 | AA | PA | i-BA | A | BA | MEK | Other products | |
| 8 | | 500 | 100.0 | 13.6 | 16.8 | 8.7 | 6.9 | 10.4 | 3.9 | 14.3 | 2.1 | 50.9 | 2.8 | 88.5 |
| 9 | 10 | 400 | 42.5 | 5.9 | 7.4 | 3.2 | 15.1 | 14.0 | 4.3 | 11.7 | 3.1 | 45.6 | 3.0 | 93.8 |
| 10 | 20 | 400 | 87.1 | 11.9 | 14.3 | 5.5 | 14.0 | 13.0 | 3.3 | 11.4 | 3.0 | 44.7 | 5.1 | 89.4 |
| 11 | 50 | 400 | 98.2 | 13.7 | 147.6 | 5.7 | 16.7 | 8.5 | 2.7 | 9.3 | 2.7 | 42.6 | 11.9 | 82.4 |
| 12 | 70 | 400 | 98.3 | 13.7 | 770.1 | 5.5 | 16.3 | 7.1 | 2.4 | 7.8 | 2.4 | 39.9 | 18.5 | 76.0 |
| 13$^{a)}$ | 10 | 400 | 31.0 | 17.1 | 16.4 | 5.6 | 15.2 | 14.1 | 3.9 | 12.1 | 2.9 | 43.9 | 2.3 | 92.1 |
| 14$^{a)}$ | | 450 | 78.0 | 40.5 | 37.5 | 5.9 | 17.1 | 10.0 | 3.2 | 13.4 | 2.5 | 43.6 | 4.3 | 89.8 |

$^{a)}$feedstock mixture composition 30% N$_2$O + 70% BBM;
C$_5$-cyclopropane derivatives;
AA - acetaldehyde;
PA - propanal;
i-BA - isobutanal;
A - acetone;
BA—butanal;
MEK—methyl ethyl ketone;
$^{b)}$total selectivity for carbonyl products (S$_\Sigma$).

TABLE 3

Gas phase oxidation of butane butylene mixtures (BBM) with different olefin contents using nitrous oxide.
Reaction conditions: flow-type reactor 25 cm$^3$, temperature 400° C., pressure 10-50 atm; feedstock mixture; 10-20 mol % N$_2$O, 90 mol % BBM; the volume flow rate of the mixture is 25 cm$^3$/min (for normal conditions)

| No | P, atm. | T, ° C. | $X_{N2O}$, % | $X_R$, % | Pr, µmol/cm$^3$ min | Pr, g/l h | Selectivity, S, % | | | | | | | Other products | $S_\Sigma^{a)}$, % |
|---|---|---|---|---|---|---|---|---|---|---|---|---|---|---|---|
| | | | | | | | C5 | AA | PA | i-BA | A | BA | MEK | | |
| Mixture 2 (olefin content 25.1 mol. %) | | | | | | | | | | | | | | | |
| 19* | 50 | 400 | 96.7 | 99.7 | 7.2 | 27.3 | 5.4 | 16.5 | 6.5 | 2.9 | 8.7 | 2.8 | 42.8 | 14.3 | 80.2 |
| Mixture 3 (olefin come a 13.2 mol. %) | | | | | | | | | | | | | | | |
| 20** | 50 | 400 | 99.9 | 93.7 | 0.8 | 3.0 | 5.4 | 17.5 | 7.1 | 2.8 | 8.3 | 2.8 | 42.3 | 13.7 | 80.8 |
| Mixture 4 (olefin content 57.6 mol. %) | | | | | | | | | | | | | | | |
| 15 | 10 | 400 | 36.2 | 7.4 | 1.6 | 6.1 | 5.1 | 14.3 | 11.1 | 2.1 | 2.7 | 5.4 | 55.6 | 3.7 | 91.2 |
| Mixture 5 (olefin content 52.7 mol. %) | | | | | | | | | | | | | | | |
| 16 | 10 | 400 | 33.2 | 7.8 | 1.5 | 6.0 | 5.2 | 11.2 | 2.9 | 3.1 | 6.9 | 4.5 | 62.1 | 4.2 | 90.7 |
| Mixture 6 (olefin content 42.3 mol. %) | | | | | | | | | | | | | | | |
| 17 | 10 | 400 | 27.3 | 7.7 | 1.2 | 4.5 | 4.4 | 18.2 | 9.1 | 1.9 | 8.4 | 3.5 | 48.3 | 6.2 | 89.4 |
| Mixture 7 (olefin content 37.9 mol. %) | | | | | | | | | | | | | | | |
| 18 | 10 | 400 | 26.2 | 8.8 | 1.2 | 4.4 | 5.5 | 21.2 | 10.2 | 1.5 | 8.3 | 3.3 | 43.3 | 6.7 | 87.8 |

*the content of nitrous oxide in the reaction mixture is 20 mol. %;
**the volume of the reactor is 125 cm$^3$;
C5 - cyclopropane derivatives;
AA - acetaldehyde;
PA is propanal;
i-BA is isobutanal;
A is acetone;
BA is butanal;
MEK - methyl ethyl ketone;
$^{a)}$the total selectivity for carbonyl products (S$_\Sigma$).

TABLE 4

Gas-phase oxidation of propane-propylene mixtures (PPM) with nitrous oxide. Reaction conditions: flow-type reactor 25 cm³, temperature 350-550° C., pressure 1-7 atm; feedstock mixture: $N_2O$ 10 mol %, PPM 90 mol %; the volume flow rate of the mixture is 25 cm³/min (for normal conditions)

| No | P, atm. | T, ° C. | $X_{N2O}$, % | $X_R$, % | Pr, μmol/cm³ min | Pr, g/l h | Selectivity, % | | | | | $S_\Sigma^{a)}$, % |
|---|---|---|---|---|---|---|---|---|---|---|---|---|
| | | | | | | | MCP | AA | PA | A | Other products | |
| 21 | 1 | 400 | 0.8 | 0.1 | 0.0 | 0.1 | 0.0 | 28.0 | 26.4 | 40.3 | 5.3 | 94.7 |
| 22 | | 450 | 3.9 | 0.6 | 0.2 | 0.6 | 2.0 | 26.7 | 24.7 | 38.3 | 8.4 | 89.7 |
| 23 | | 500 | 13.9 | 2.2 | 0.6 | 2.0 | 4.7 | 24.0 | 22.6 | 36.4 | 12.5 | 83 |
| 24 | | 550 | 42.1 | 5.9 | 1.4 | 4.5 | 2.0 | 24.1 | 14.0 | 32.5 | 27.4 | 70.6 |
| 25 | 4 | 350 | 2.4 | 4 | 0.1 | 0.3 | 3.3 | 37.2 | 16.8 | 32.7 | 10.0 | 86.7 |
| 26 | | 400 | 14.8 | 2.3 | 0.7 | 2.1 | 5.3 | 28.9 | 18.6 | 35.2 | 12.0 | 82.7 |
| 27 | | 450 | 46.4 | 7.9 | 2.0 | 6.4 | 5.0 | 21.9 | 18.3 | 33.1 | 21.7 | 73.3 |
| 28 | 7 | 350 | 8.8 | 1.3 | 0.4 | 1.2 | 4.8 | 35.2 | 15.3 | 32.5 | 12.1 | 83 |
| 29 | | 400 | 28.4 | 4.7 | 1.3 | 4.0 | 6.0 | 27.2 | 17.4 | 33.9 | 15.5 | 78.5 |
| 30 | | 450 | 74.5 | 12.5 | 3.2 | 10.3 | 6.1 | 21.3 | 16.5 | 36.8 | 19.2 | 74.6 |

MCP - methylcyclopropane;
AA - acetaldehyde;
PA - propanal;
A - acetone;
$^{a)}$total selectivity for carbonyl products ($S_\Sigma$).

The invention claimed is:

1. A process for producing $C_2$-$C_4$ carbonyl compounds from $C_2$-$C_4$ olefins, characterized in that said process for producing $C_2$-$C_4$ carbonyl compounds, is carried out in a gas phase by reacting nitrous oxide with a mixture of aliphatic $C_2$-$C_4$ olefins and alkanes at a temperature of 300-550° C. and pressure of 1-100 atm.

2. The process of claim 1, wherein gaseous fractionation products of thermal and/or catalytic cracking process are used as a starting alkane-olefin mixture with no preliminary isolation of the individual olefins from the fractionation products.

3. The process of claim 1, herein a butane-butylene fraction of thermal and/or catalytic cracking process is used as the starting alkane-olefin mixture.

4. The process of claim 1, wherein a propane-propylene fraction of thermal and/or catalytic cracking process is used as the starting alkane-olefin mixture.

5. The process of claim 1, wherein a fraction of thermal and/or catalytic cracking process enriched in ethylene is used as the starting alkane-olefin mixture.

6. The process of claim 1, wherein a butane-butene mixture enriched in butene-2 is used as the starting alkane-olefin mixture.

7. The process of claim 1, wherein a mixture comprising $C_2$ and/or $C_3$ and/or $C_4$ olefins with $C_1$ and/or $C_2$ and/or $C_3$ and/or $C_4$ alkanes in any ratios is used as the starting alkane-olefin mixture.

8. The process of claim 1, wherein the starting alkane-olefin mixture may comprise other hydrocarbons as impurities caused by the method of preparation of said mixture.

9. The process of claim 1, wherein the nitrous oxide may comprise other gases, the presence of which is associated with the method for its preparation.

10. The process of claim 1, wherein the oxidation process of the alkane-olefin mixture is carried out in a single flow-type reactor, without recycling the reaction mixture, with nitrous oxide conversion being at least 90%.

11. The process of claim 1, wherein in order to achieve an olefin conversion of at least 90%, the oxidation of the alkane-olefin mixture is carried out in several stages using several oxidation reactors with independent feeding of nitrous oxide at each stage, and the reaction products are isolated from the reaction mixture after each oxidation reactor.

12. The process of claim 1, wherein in order to achieve an olefin conversion of at least 90%, the oxidation process of the alkane-olefin mixture is carried out in several stages using several oxidation reactors with independent feeding of nitrous oxide at each stage, and with intermediate partial cooling of the reaction mixture, but with no isolation of the reaction products from the reaction mixture after the intermediate oxidation reactors.

13. The process according to claim 1, wherein the $C_2$-$C_4$ carbonyl compounds are selected from $C_2$-$C_4$ aldehydes and ketones.

14. The process according to claim 10, wherein the nitrous oxide conversion is 99%.

15. The process according to claim 10, wherein the nitrous oxide conversion is complete.

* * * * *